US012702573B2

(12) United States Patent
Ouyang

(10) Patent No.: US 12,702,573 B2
(45) Date of Patent: Aug. 11, 2026

(54) PLACING AND REMOVING SURGICAL STENTS

(71) Applicant: MICRONVISION CORP., Bellevue, WA (US)

(72) Inventor: Xiaolong Ouyang, Bellevue, WA (US)

(73) Assignee: MicronVision Corp., Bellevue, WA (US)

( * ) Notice: Subject to any disclaimer, the term of this patent is extended or adjusted under 35 U.S.C. 154(b) by 954 days.

(21) Appl. No.: 16/972,989

(22) PCT Filed: Jun. 7, 2019

(86) PCT No.: PCT/US2019/036060

§ 371 (c)(1),
(2) Date: Dec. 7, 2020

(87) PCT Pub. No.: WO2019/237003

PCT Pub. Date: Dec. 12, 2019

(65) Prior Publication Data

US 2021/0251789 A1 Aug. 19, 2021

Related U.S. Application Data

(63) Continuation-in-part of application No. 16/363,209, filed on Mar. 25, 2019, now Pat. No. 11,832,797.
(Continued)

(51) Int. Cl.
*A61F 2/966* (2013.01)
*A61B 1/00* (2006.01)
(Continued)

(52) U.S. Cl.
CPC .......... *A61F 2/966* (2013.01); *A61B 1/00052* (2013.01); *A61B 1/00066* (2013.01);
(Continued)

(58) Field of Classification Search
CPC ..... A61F 2/966; A61F 2002/9528; A61B 1/05
See application file for complete search history.

(56) References Cited

U.S. PATENT DOCUMENTS

| | | | |
|---|---|---|---|
| 4,854,302 | A | 8/1989 | Allred, III |
| 4,979,497 | A | 12/1990 | Matsura |

(Continued)

FOREIGN PATENT DOCUMENTS

| | | |
|---|---|---|
| CN | 102858275 | 1/2013 |
| EP | 1690512 | 8/2006 |

(Continued)

OTHER PUBLICATIONS

International Search Report and Written Opinion of PCT/US2016/18670, dated Jul. 12, 2016.

(Continued)

*Primary Examiner* — Elizabeth Houston
*Assistant Examiner* — Jonathan A Hollm
(74) *Attorney, Agent, or Firm* — Wissing Miller LLP

(57) ABSTRACT

Systems and methods are configured for precise placement of surgical stents. A customized endoscopic system has a stent positioned between an inner cannula and the outer sleeve. The inner cannula has an integrated camera and illumination on its distal tip. The operator can make precise stent placements while viewing live video on an integrated display mounted on the hand piece. The stent can be removed using a specialized hook device. The system can have a single use portion that includes the cannula with imaging module, stent and outer sleeve. The re-usable portion can include the hand piece and display screen.

17 Claims, 17 Drawing Sheets

Related U.S. Application Data

(60) Provisional application No. 62/816,366, filed on Mar. 11, 2019, provisional application No. 62/688,397, filed on Jun. 22, 2018, provisional application No. 62/686,680, filed on Jun. 19, 2018, provisional application No. 62/686,682, filed on Jun. 19, 2018, provisional application No. 62/682,854, filed on Jun. 9, 2018, provisional application No. 62/681,824, filed on Jun. 7, 2018, provisional application No. 62/681,687, filed on Jun. 7, 2018.

(51) Int. Cl.
*A61B 1/05* (2006.01)
*A61B 1/06* (2006.01)
*A61F 2/95* (2013.01)

(52) U.S. Cl.
CPC ...... *A61B 1/00087* (2013.01); *A61B 1/00154* (2013.01); *A61B 1/05* (2013.01); *A61B 1/0676* (2013.01); *A61F 2002/9528* (2013.01)

(56) References Cited

U.S. PATENT DOCUMENTS 5,010,876 A 4/1991 Henley
5,188,093 A 2/1993 Lafferty
5,281,214 A 1/1994 Wilkins
5,323,767 A 6/1994 Lafferty
5,329,936 A 7/1994 Lafferty
5,486,155 A 1/1996 Muller
5,549,547 A 8/1996 Cohen
5,569,163 A 10/1996 Francis
5,666,561 A 9/1997 Stephenson
5,667,472 A 9/1997 Finn
5,667,476 A 9/1997 Frassica et al.
5,785,644 A 7/1998 Grabover
5,860,953 A 1/1999 Snoke
5,873,814 A 2/1999 Adair
5,928,137 A 7/1999 Green
5,935,141 A 8/1999 Weldon
5,957,947 A 9/1999 Wattiez
6,007,531 A 12/1999 Snoke
6,007,546 A 12/1999 Snow
6,017,322 A 1/2000 Snoke
6,033,378 A 3/2000 Lundquist
6,059,719 A 5/2000 Yamamato et al.
6,095,970 A 8/2000 Hidaka
6,174,307 B1 1/2001 Daniel
6,210,416 B1 4/2001 Chu
6,211,904 B1 4/2001 Adair
6,221,007 B1 4/2001 Green
6,221,070 B1 4/2001 Tu et al.
6,261,226 B1 7/2001 McKenna
6,280,386 B1 8/2001 Alfano
6,331,174 B1 12/2001 Reinhard
6,387,043 B1 5/2002 Yoon
6,398,743 B1 6/2002 Halseth
6,507,699 B2 1/2003 Lemoine
6,518,823 B1 2/2003 Kawai
6,793,882 B1 9/2004 Verschuur
6,917,380 B1 7/2005 Tay
7,256,446 B2 8/2007 Hu
7,428,378 B1 9/2008 Warpakowski
7,507,205 B2 3/2009 Borovsky
7,591,799 B2 9/2009 Selkee
7,606,609 B2 10/2009 Muranushi
7,780,650 B2 8/2010 Frassica
7,798,995 B2 9/2010 Yue
7,931,616 B2 4/2011 Selkee
7,946,981 B1 5/2011 Cubb
8,052,609 B2 11/2011 Harhen
8,057,464 B2 11/2011 Chen
8,187,171 B2 5/2012 Irion
8,197,398 B2 6/2012 Scholly
8,235,975 B2 8/2012 Chen
8,361,775 B2 1/2013 Flower
8,460,182 B2 6/2013 Ouyang
8,523,808 B2 9/2013 Selkee
8,696,552 B2 4/2014 Whitman
8,803,960 B2 8/2014 Sonnenschein
8,834,357 B2 9/2014 Oskin
8,845,522 B2 9/2014 McIntyre
8,952,312 B2 2/2015 Blangart
8,998,844 B2 4/2015 Reed
9,649,014 B2 5/2017 Ouyang
9,736,342 B2 8/2017 Mueckl
9,895,048 B2 2/2018 Ouyang
10,278,563 B2 5/2019 Ouyang
10,292,571 B2 5/2019 Ouyang
2001/0007051 A1 7/2001 Nakashima
2001/0049509 A1 12/2001 Sekine
2002/0120277 A1* 8/2002 Hauschild ................ A61F 2/95 606/108
2003/0016284 A1 1/2003 Squilla
2003/0023142 A1 1/2003 Grabover
2003/0078476 A1 4/2003 Hill
2003/0078502 A1 4/2003 Miyaki
2003/0151680 A1 8/2003 McDermott
2003/0199735 A1 10/2003 Dickopp
2004/0054254 A1 3/2004 Miyake
2004/0054259 A1 3/2004 Hasegawa
2004/0138558 A1 7/2004 Dunki-Jacobs
2004/0162572 A1 8/2004 Sauer
2005/0010178 A1 1/2005 Katz
2005/0049459 A1 3/2005 Hern
2005/0085695 A1 4/2005 Sherner
2005/0154262 A1 7/2005 Banik
2005/0159646 A1 7/2005 Nordstrom
2005/0177027 A1 8/2005 Hirata
2005/0264687 A1 12/2005 Murayama
2005/0277874 A1 12/2005 Selkee
2005/0277875 A1 12/2005 Selkee
2006/0052710 A1 3/2006 Miura
2006/0063976 A1 3/2006 Aizenfeld
2006/0114986 A1 6/2006 Knapp
2006/0152601 A1 7/2006 Parekh
2006/0167340 A1 7/2006 Peas
2006/0171693 A1 8/2006 Todd
2006/0173245 A1 8/2006 Todd
2006/0184227 A1 8/2006 Rust
2006/0259124 A1 11/2006 Matsuoka
2006/0287576 A1 12/2006 Tsuji
2007/0060789 A1 3/2007 Uchimura
2007/0081920 A1 4/2007 Murphy
2007/0117437 A1 5/2007 Boehnlein
2007/0123971 A1* 5/2007 Kennedy .................. A61F 2/95 623/1.11
2007/0129604 A1 6/2007 Hatcher
2007/0162095 A1 7/2007 Kimmel
2007/0167678 A1 7/2007 Moskowitz
2007/0167868 A1 7/2007 Sauer
2007/0173693 A1 7/2007 Refael
2007/0188604 A1 8/2007 Miyamoto
2007/0197875 A1 8/2007 Osaka
2007/0210162 A1 9/2007 Keen
2007/0225556 A1 9/2007 Ortiz
2007/0238927 A1 10/2007 Ueno
2008/0004642 A1 1/2008 Birk
2008/0071144 A1 3/2008 Kimmel
2008/0097550 A1 4/2008 Dicks
2008/0108869 A1 5/2008 Sanders
2008/0195125 A1 8/2008 Orbay
2008/0195128 A1 8/2008 Orbay
2008/0225410 A1 9/2008 Ning
2008/0234547 A1 9/2008 Irion et al.
2008/0255416 A1 10/2008 Gilboa
2008/0262306 A1 10/2008 Kawai
2008/0300456 A1 12/2008 Irion
2009/0027489 A1 1/2009 Takemura
2009/0065565 A1 3/2009 Lemoine
2009/0076321 A1 3/2009 Suyama
2009/0076328 A1 3/2009 Root
2009/0080214 A1 3/2009 Watanabe

(56) References Cited

U.S. PATENT DOCUMENTS

2009/0105538 A1 4/2009 Van Dam
2009/0118580 A1 5/2009 Sun
2009/0118641 A1 5/2009 Van Dam
2009/0149713 A1 6/2009 Niida
2009/0225159 A1 9/2009 Schneider
2009/0227897 A1 9/2009 Wendt
2009/0286412 A1 11/2009 Ikeda
2009/0287663 A1 11/2009 Takeuchi
2010/0026201 A1 2/2010 Byun et al.
2010/0069834 A1 3/2010 Schultz
2010/0094216 A1 4/2010 Yue
2010/0095969 A1 4/2010 Schwartz
2010/0101569 A1 4/2010 Kim
2010/0121142 A1 5/2010 Ouyang
2010/0157039 A1 6/2010 Sugai
2010/0160914 A1 6/2010 Bastian
2010/0168827 A1 7/2010 Schultz
2010/0191051 A1 7/2010 Miyake
2010/0191053 A1 7/2010 Garcia
2010/0234736 A1 9/2010 Corl
2011/0009694 A1 1/2011 Schultz
2011/0034769 A1 2/2011 Adair
2011/0037876 A1 2/2011 Talbert
2011/0054446 A1 3/2011 Schultz
2011/0092775 A1 4/2011 Deshmukh
2011/0105839 A1 5/2011 Hoffman
2011/0112622 A1 5/2011 Phan
2011/0130627 A1 6/2011 McGrail
2011/0211115 A1 9/2011 Tsai
2011/0213206 A1 9/2011 Boutillette
2011/0245602 A1 10/2011 Brannon
2011/0264191 A1 10/2011 Rothstein
2011/0288482 A1 11/2011 Farrell
2012/0016191 A1 1/2012 Ito
2012/0040305 A1 2/2012 Karazivan
2012/0041533 A1 2/2012 Bertolino
2012/0053515 A1 3/2012 Crank
2012/0083877 A1* 4/2012 Nguyen ................ A61F 2/2418 623/2.11
2012/0100729 A1* 4/2012 Edidin ................ H01R 13/622 439/38
2012/0165916 A1 6/2012 Jordan
2012/0178991 A1 7/2012 Clark
2012/0226103 A1 9/2012 Gunday
2012/0236138 A1 9/2012 Liu
2012/0245242 A1 9/2012 Peiffer
2012/0245418 A1 9/2012 Boulais
2012/0253116 A1 10/2012 Sniffin
2012/0259203 A1 10/2012 Devereux
2012/0286020 A1 11/2012 Smith
2012/0289858 A1 11/2012 Ouyang
2013/0035553 A1 2/2013 Kongstorum
2013/0046142 A1 2/2013 Remijan
2013/0057667 A1 3/2013 McGrath
2013/0150672 A1 6/2013 Fujitani
2013/0172676 A1 7/2013 Levy
2013/0225921 A1 8/2013 Liu
2013/0253402 A1 9/2013 Badawi
2013/0289559 A1 10/2013 Reid
2013/0324973 A1 12/2013 Reed
2013/0345514 A1 12/2013 Manion
2014/0022649 A1 1/2014 Echhardt
2014/0107416 A1 4/2014 Bimkrant
2014/0111634 A1 4/2014 Mueckl
2014/0154399 A1 6/2014 Weikart
2014/0180007 A1 6/2014 Edidin
2014/0188211 A1 7/2014 Roeder
2014/0213848 A1 7/2014 Moskowitz
2014/0228635 A1 8/2014 Tuliakov
2014/0275763 A1 9/2014 King
2014/0296866 A1 10/2014 Salman
2014/0323991 A1 10/2014 Tang
2015/0005575 A1 1/2015 Kobayashi
2015/0011830 A1 1/2015 Hunter
2015/0018622 A1 1/2015 Tesar
2015/0018710 A1 1/2015 Furlong
2015/0150441 A1 6/2015 Ouyang
2015/0164313 A1 6/2015 Oyuang
2015/0196197 A1 7/2015 Kienzle
2015/0238251 A1 8/2015 Shikhman
2015/0297311 A1 10/2015 Tesar
2016/0073853 A1 3/2016 Venkatesan et al.
2016/0077008 A1 3/2016 Takasu
2016/0174819 A1 6/2016 Ouyang
2016/0334694 A1 11/2016 Liu
2016/0367119 A1 12/2016 Ouyang
2017/0086651 A1 3/2017 Sato
2017/0188793 A1 7/2017 Ouyang
2017/0188795 A1 7/2017 Ouyang
2017/0215699 A1 8/2017 Ouyang
2017/0295347 A1 10/2017 Schneider
2017/0310858 A1 10/2017 Mueckl
2018/0132700 A1 5/2018 Ouyang
2018/0184892 A1 7/2018 Truckai
2018/0235441 A1 8/2018 Huang
2018/0256009 A1 9/2018 Ouyang
2019/0029497 A1 1/2019 Mirza
2019/0142262 A1 5/2019 Inglis
2019/0216325 A1 7/2019 Ouyang
2019/0223691 A1 7/2019 Takatsuji
2019/0246873 A1 8/2019 Lu
2019/0246884 A1 8/2019 Lu et al.
2019/0282073 A1 9/2019 Truckai
2019/0320879 A1 10/2019 Langell
2019/0374095 A1 12/2019 Lord
2020/0204776 A1 6/2020 Themelis
2020/0214739 A1 7/2020 Shi
2020/0275827 A1 9/2020 Weise
2021/0228806 A1 7/2021 Streeter
2021/0401277 A1 12/2021 Ouyang

FOREIGN PATENT DOCUMENTS

EP 2560589 4/2010
EP 3384879 4/2011
EP 2749258 7/2014
EP 3078354 10/2016
JP 2009148420 7/2009
WO 2011133792 10/2011
WO 2012060932 5/2012
WO 2014031192 2/2014
WO 2014065901 5/2015
WO 2016032729 3/2016
WO 2016040131 3/2016
WO 2016137838 9/2016
WO 2018136950 7/2018
WO 2019237003 12/2019

OTHER PUBLICATIONS

International Search Report and Written Opinion of PCT/US2018/014880, dated Jun. 6, 2018.
International Search Report and Written Opinion of PCT/US2018/065396, dated Feb. 24, 2017.
International Search Report and Written Opinion of PCT/US2021/050095 dated Dec. 17, 2021.
International Search Report and Written Opinion of PCT/US2019/036060 dated Aug. 27, 2019.
International Search Report and Written Opinion of PCT/US2017/053171 mailed Dec. 5, 2017.
International Preliminary Report on Patentability of PCT/US2017/053171 completed on Jul. 1, 2019.
Extended European Search Report of European Patent Application No. EP19816177 dated Feb. 15, 2022.
International Search Report for PCT/US2019/036060, dated Aug. 27, 2019.
Extended European Search Report of European Patent Application No. EP19816177 completed Feb. 2, 2022.

* cited by examiner 174
172
170
160
422
110
420
130
176
120

174
172
170
160
422
110
420
420
130
176
120

170
174
172
160
422
110
420
130
176
120

130
174
172
420
230
242
140
440

160
110
1220
420
710
1210
810
422
720

160
710
720
1210
720
1210
1220

720
1210
1210
810
720

110
1220
420
1212
422

PLACING AND REMOVING SURGICAL STENTS

REFERENCE TO RELATED APPLICATIONS

This patent application claims the benefit of and incorporates by reference each of the following provisional applications:

U.S. Prov. Ser. No. 62/688,397 filed Jun. 22, 2018;
U.S. Prov. Ser. No. 62/686,682 filed Jun. 19, 2018;
U.S. Prov. Ser. No. 62/686,680 filed Jun. 19, 2018;
U.S. Prov. Ser. No. 62/682,854 filed Jun. 9, 2018;
U.S. Prov. Ser. No. 62/681,824 filed Jun. 7, 2018; and
U.S. Prov. Ser. No. 62/681,687 filed Jun. 7, 2018.

This patent application is also related to and incorporates by reference each of the following international, non-provisional and provisional applications:

U.S. patent application Ser. No. 16/363,209 filed Mar. 25, 2019;
International Patent Application No. PCT/US17/53171 filed Sep. 25, 2017;
U.S. Prov. Ser. No. 62/816,366 filed Mar. 11, 2019;
U.S. Prov. Ser. No. 62/671,445 filed May 15, 2018;
U.S. Prov. Ser. No. 62/654,295 filed Apr. 6, 2018;
U.S. Prov. Ser. No. 62/647,817 filed Mar. 25, 2018;
U.S. Prov. Ser. No. 62/558,818 filed Sep. 14, 2017;
U.S. Prov. Ser. No. 62/550,581 filed Aug. 26, 2017;
U.S. Prov. Ser. No. 62/550,560 filed Aug. 25, 2017;
U.S. Prov. Ser. No. 62/550,188 filed Aug. 25, 2017;
U.S. Prov. Ser. No. 62/502,670 filed May 6, 2017;
U.S. Prov. Ser. No. 62/485,641 filed Apr. 14, 2017;
U.S. Prov. Ser. No. 62/485,454 filed Apr. 14, 2017;
U.S. Prov. Ser. No. 62/429,368 filed Dec. 2, 2016;
U.S. Prov. Ser. No. 62/428,018 filed Nov. 30, 2016;
U.S. Prov. Ser. No. 62/424,381 filed Nov. 18, 2016;
U.S. Prov. Ser. No. 62/423,213 filed Nov. 17, 2016;
U.S. Prov. Ser. No. 62/405,915 filed Oct. 8, 2016;
U.S. Prov. Ser. No. 62/399,712 filed Sep. 26, 2016;
U.S. Prov. Ser. No. 62/399,436 filed Sep. 25, 2016;
U.S. Prov. Ser. No. 62/399,429 filed Sep. 25, 2016;
U.S. Prov. Ser. No. 62/287,901 filed Jan. 28, 2016;
U.S. Prov. Ser. No. 62/279,784 filed Jan. 17, 2016;
U.S. Prov. Ser. No. 62/275,241 filed Jan. 6, 2016;
U.S. Prov. Ser. No. 62/275,222 filed Jan. 5, 2016;
U.S. Prov. Ser. No. 62/259,991 filed Nov. 25, 2015;
U.S. Prov. Ser. No. 62/254,718 filed Nov. 13, 2015;
U.S. Prov. Ser. No. 62/139,754 filed Mar. 29, 2015;
U.S. Prov. Ser. No. 62/120,316 filed Feb. 24, 2015; and
U.S. Prov. Ser. No. 62/119,521 filed Feb. 23, 2015.

All of the above-referenced non-provisional, provisional and international patent applications are collectively referenced herein as "the commonly assigned incorporated applications."

FIELD

This patent specification generally relates mainly to a medical device for use in placing and retrieving surgical stents. More particularly, some embodiments relate to devices and methods using endoscopy for placing and removing prostatic stents.

BACKGROUND

There are many medical procedures for placing a stent inside a human body, such as blood vessels or urinary tracts. In the case of a prostatic stent, a stent is used to keep open the male urethra and allow the passing of urine in cases of prostatic obstruction and lower urinary tract symptoms. Conventional systems for placing any stents are believed to be cumbersome, inefficient and can cause local trauma and/or substantial patient discomfort. Many conventional stent placement procedures are carried out with medical equipment that is not specialized and/or customized for a particular application. For example, in the case of prostatic stents, it is common to deploy the stent using a complex, conventional, general purpose endoscopic device that has a rigid cannula, made of stainless steel, having an outer diameter of 7 mm or greater (21 fr.). Such systems are expensive, complicated and can cause significant discomfort and/or local trauma for the patient.

The subject matter described or claimed in this patent specification is not limited to embodiments that solve any specific disadvantages or that operate only in environments such as those described above. Rather, the above background is only provided to illustrate one exemplary technology area where some embodiments described herein may be practiced.

SUMMARY

According to some embodiments, an endoscope for deploying a tubular endoscope in a passage in a patient comprises: a handle 140 configured to be grasped by a user, a shaft 172 extending distally relative to the handle; an outer sleeve 422 extending distally from the shaft; an inner cannula 420 configured to fit within the outer sleeve for relative sliding motion therebetween; and a collar or catch 170 coupled with the outer sleeve and configured to move together therewith between a distal position in which distal ends of the inner cannula and the outer sleeve align and a proximal position by which a distal portion of the inner cannula protrudes distally from the outer sleeve. The distal portion of the inner cannula and a distal portion of the outer sleeve are dimensioned to allow a tubular radial space therebetween, which radial space is configured to constrain a radially expandable stent 160 in a compressed state and said distal portion of the inner cannula being configured to engage the stent to prevent proximal motion but allow distal motion of the stent relative to the inner cannula. The tubular space matches the stent in length such that when the outer sleeve is at its proximal position the stent is not constrained by said outer sleeve and can expand radially to an expanded state and remain in said passage. A camera module 810 at the distal end of said inner cannula is configured to view the passage and a video screen 150 attached to and mechanically supported by said handle is configured to show images of the passage and of the stent being deployed therein. The shaft, collar, outer sleeve and cannula form a single-use stent-deployment portion of the endoscope and the handle and video screen form a reusable portion. These two portions are configured to connect and disconnect through connectors that mate and release by hand, without tools, for assembly of the two portions into an endoscope and for disposal of the single-use portion after use thereof in a patient procedure.

In some embodiments, for removal of a stent deployed in a passage in the patient the endoscope further comprises a single-use stent removal portion with electrical and mechanical connectors for removable attachment to said handle, in place of the stent deployment portion. The stent removal portion differs from said stent deployment portion by including plural hooks at a distal part of the inner cannula, which hooks are configured to fit in said tubular space when the outer cannula is in its distal position and to expand radially as the outer sleeve moves to its proximal position and to engage loops at a proximal portion of said stent. The stent removal portion is configured to draw said stent proximally into said tubular space as the outer sleeve moves from its distal to its proximal positions.

Each of the single-use portion for deploying a stent and the single-use portion for removing a stent further comprises a housing 174 that has a proximal end connecting to said handle, a distal end connecting to said shaft, and an annular space in which a proximal portion of the shaft moves between said distal and proximal positions of the shaft, in some embodiments. The inner cannula is in a fixed position relative to the handle when said single-use and multiple-use portion are assembled into said endoscope, in some embodiments. The endoscope further includes proximal and distal ports in said outer sleeve and a fluid conduit through which fluid moves within and along a length of said outer sleeve between said ports, according to some embodiments. The inner cannula has a distal end stepped down in diameter to engage a matching diameter distal end of the stent to thereby prevent proximal motion but allow distal motion of the stent relative to the inner cannula, according to some embodiments. At least distal portions of the outer sleeve and the inner cannula are sufficiently flexible to bend when being inserted in curving portions of said passage, according to some embodiments.

According to some embodiment, an endoscope comprises: a handle 140 configured to be grasped by a user; a shaft 172 extending distally relative to the handle; an outer sleeve 422 extending distally from the shaft; and an inner cannula 420 configured to fit within the outer sleeve. The outer sleeve is configured to move relative to the handle and the inner cannula between a distal position and a proximal position. When the outer sleeve is in its proximal position a distal portion of the inner cannula protrudes distally from the outer sleeve and when the outer sleeve is in its distal position a tubular stent fits in a tubular space between distal portions of the outer sleeve and the inner cannula. A camera module 810 at the distal end of said inner cannula views the passage and a video screen 150 attached to and mechanically supported by said handle shows images of the passage and of the stent being deployed therein. The shaft, collar, outer sleeve and cannula form a single-use stent-deployment portion of the endoscope and the handle and video screen form a reusable portion. The two portions connect through connectors that mate and release by hand, without tools, to assemble the two portions into said endoscope and for disposal of said single-use portion after use thereof in a patient procedure.

For removing a stent from a passage in a patient, a single-use stent removal portion is configured to removably attach to said handle, in place of the stent deployment portion, and differs from said stent deployment portion by including plural hooks at a distal end of the inner cannula, which hooks are configured to fit between the inner cannula and the outer sleeve when the outer sleeve is in its distal position and to expand radially as the outer sleeve moves to its proximal position and to engage loops at a proximal portion of said stent. The stent removal portion is configured to draw said stent proximally into said tubular space as the outer sleeve moves from its distal to its proximal positions.

Each of the single-use portions further comprises a housing 174 that has a proximal end connecting to said handle, a distal end connecting to said shaft, and an annular space in which a proximal portion of the shaft moves between said distal and proximal position of the shaft, in some embodiments. Proximal and distal ports in said outer sleeve and a fluid conduit through which fluid moves within and along a length of said outer sleeve between said ports are provided, according to some embodiments. The inner cannula has a distal end stepped down in diameter to engage a matching diameter distal end of the stent to thereby prevent proximal motion but allow distal motion of the distal end of the stent relative to the inner cannula, according to some embodiments. At least distal portions of the outer sleeve and the inner cannula are sufficiently flexible to bend when being inserted in curving portions of said passage, according to some embodiments.

According to some embodiments, a method of deploying a stent in a passage in a patient and/or removing the stent comprises: placing a tubular stent in a compressed state in a tubular space between distal portions of an inner cannula and an outer sleeve of an endoscope such that the stent engages the inner cannula to prevent proximal motion but allow distal motion of the stent relative to the inner cannula; releasably securing said outer sleeve and inner cannula to a handle configured to be grasped by a user; inserting the outer sleeve in a passage in the patient's body, with the stent in said tubular space between the outer sleeve and the inner cannula; moving the outer sleeve proximally relative to the inner cannula, the stent, and the handle to thereby free the stent of being radially constrained by the outer sleeve and allow the stent to expand radially to an expanded state and remain in the passage in the patient; withdrawing the inner cannula from the patient; and imaging the passage with a video camera at a tip of the inner cannula while inserting the outer sleeve, moving the outer sleeve proximally relative to the inner cannula, and withdrawing the inner cannula, and displaying the images on a video screen secured to and mechanically supported by said handle. Moving the outer sleeve proximally includes moving a proximal portion of the sleeve within an annular space of a housing releasably secured to said handle, according to some embodiments. The method includes connecting said outer sleeve, inner cannula and housing to said handle through electrical and mechanical connectors that connect and disconnect by hand, without tools, according to some embodiments.

According to some embodiments, the method further includes removing a stent that has expanded radially and has remained in the passage by inserting an outer sleeve into the passage while viewing the passage with a video camera at a distal tip of an inner cannula that is in the outer sleeve, moving the outer sleeve proximally relative to the inner cannula to allow hook secured to the inner cannula to expand radially, engaging loops at a proximal portion of the stent with said hooks, moving one or both of the inner cannula and the outer sleeve relative to the other to draw the stent into a tubular space between distal portions of the outer sleeve and the inner cannula, and withdrawing the outer sleeve, the inner cannula, and the stent from the passage.

According to some embodiments, an alternative method of removing a stent that has expanded radially and has remained in the passage comprises inserting an outer sleeve into the passage while viewing the passage with a video camera at a distal tip of an inner cannula that is in the outer sleeve, moving the outer sleeve proximally relative to the inner cannula to allow hook secured to the inner cannula to expand radially, engaging loops at a proximal portion of the stent with said hooks, and moving said inner cannula proximally relative to the passage to remove said stent from the passage.

As used herein, the grammatical conjunctions "and", "or" and "and/or" are all intended to indicate that one or more of the cases, object or subjects they connect may occur or be present. In this way, as used herein the term "or" in all cases indicates an "inclusive or" meaning rather than an "exclusive or" meaning.

As used herein the terms "surgical" or "surgery" refer to any physical intervention on a patient's tissues, and does not necessarily involve cutting a patient's tissues or closure of a previously sustained wound.

BRIEF DESCRIPTION OF THE DRAWINGS

To further clarify the above and other advantages and features of the subject matter of this patent specification, specific examples of embodiments thereof are illustrated in the appended drawings. It should be appreciated that these drawings depict only illustrative embodiments and are therefore not to be considered limiting of the scope of this patent specification or the appended claims. The subject matter hereof will be described and explained with additional specificity and detail through the use of the accompanying drawings in which:

DETAILED DESCRIPTION

A detailed description of examples of preferred embodiments is provided below. While several embodiments are described, it should be understood that the new subject matter described in this patent specification is not limited to any one embodiment or combination of embodiments described herein, but instead encompasses numerous alternatives, modifications, and equivalents. In addition, while numerous specific details are set forth in the following description in order to provide a thorough understanding, some embodiments can be practiced without some or all of these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features of other described embodiments or with other features. Further, like reference numbers and designations in the various drawings indicate like elements.

Figures 1, 2:
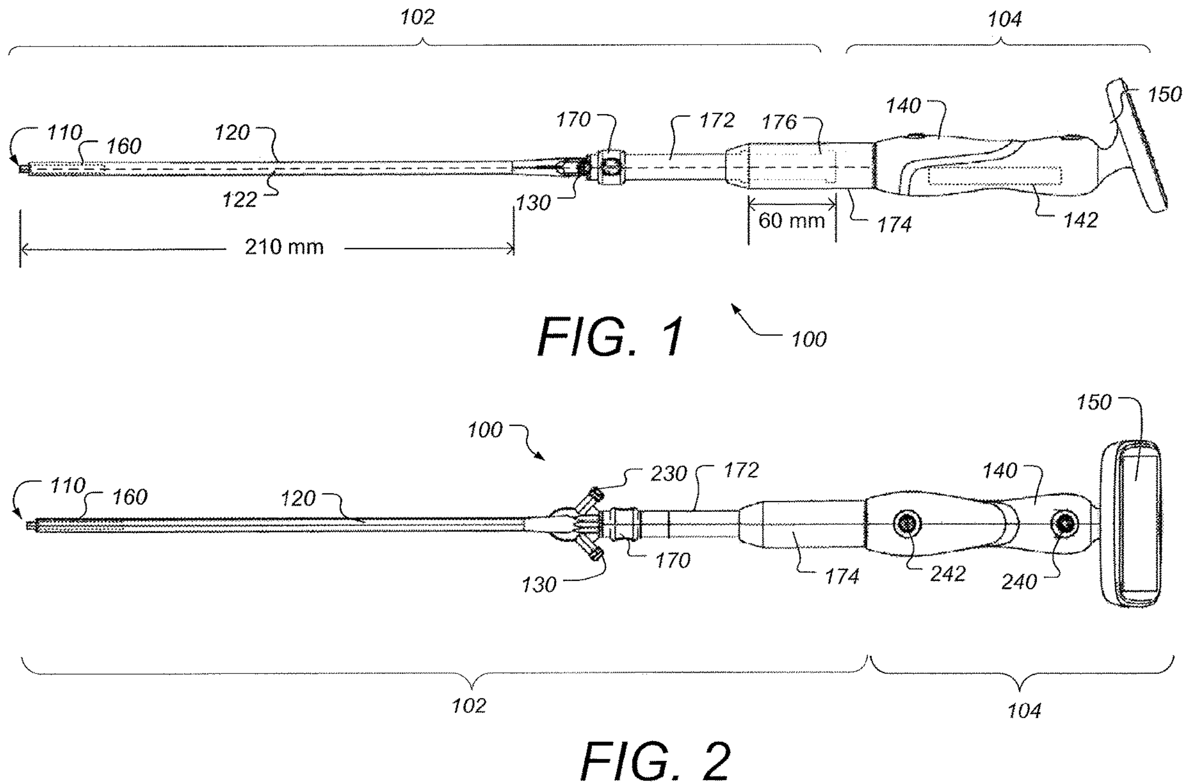
FIGS. 1, 2 and 3 are side, top and perspective views of an endoscopic system configured to deploy a surgical stent, according to some embodiments.
Figure 3:
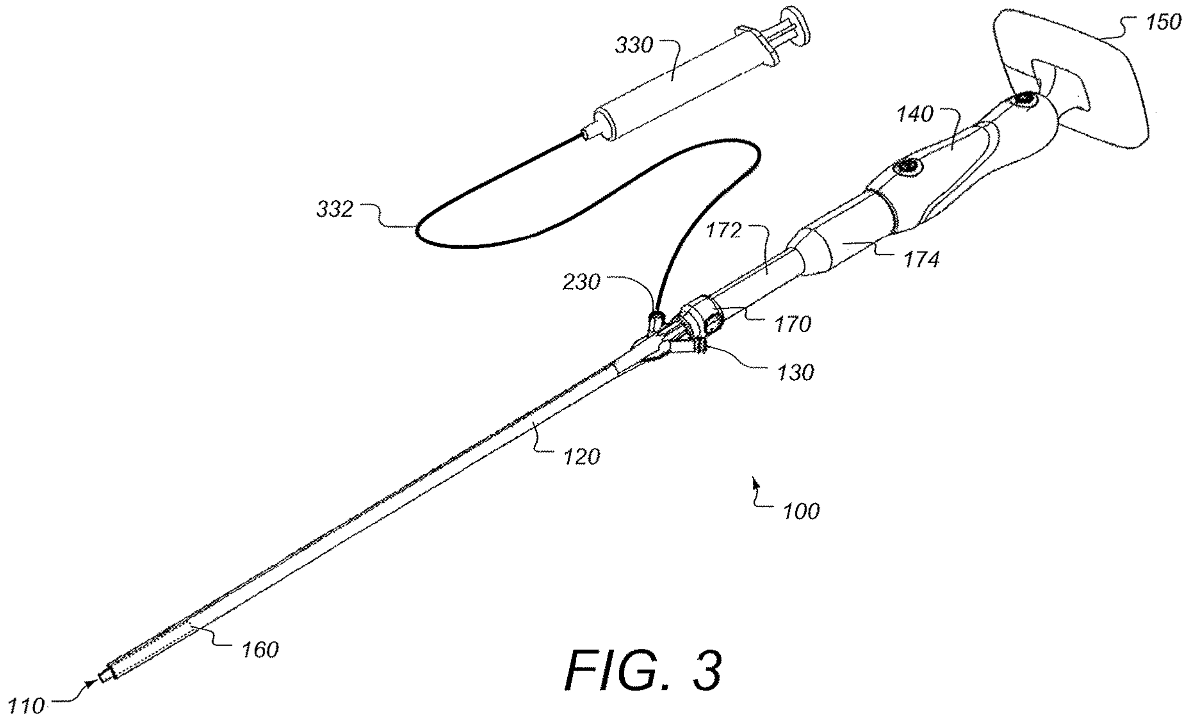

FIGS. 1, 2 and 3 are side, top and perspective views of an endoscopic system configured to deploy a surgical stent, according to some embodiments. System 100 is configured for minimally invasive and precise placement of a surgical stents. System 100 is adapted for easy and quick use with minimized patient discomfort and high placement accuracy. According to some embodiments, the system 100 includes a semi-rigid endoscope having an integrated stent 160 and dual cannula 120. Dual cannula 120 includes in inner cannula that has an imaging and illumination modules on its distal tip 110, and an outer sleeve. The outer sleeve is configured such that it can slide longitudinally with respect to the inner cannula. An electrical cable 122 is positioned within the inner cannula and supplies control signals and power to the camera and LED illumination modules on distal tip 110 and also transmits video image data from the camera module to the hand piece 140 and display 150 for viewing by an operator. In the example shown, hand piece 140 includes two control buttons 240 and 242 which can be configured for power on/off and image capture, respectively. According to some embodiments, hand piece 140 includes a rechargeable battery 142 as well as electronics or video capture, processing and display on or in display 150.

The cannula 120 is connected proximally to a fluid hub including in this example two fluid ports 130 and 230. Proximal to the fluid hub is a shaft 172 and a collar 170. According to some embodiments, the collar 170 is fixed to the outer sleeve of cannula 120 such that it can be used to retract and extend the outer sleeve relative to the inner cannula and stent 160 as will be shown and described further herein. Shaft 172 can slide into housing 174. Dashed outline 176 illustrates the position of shaft 172 in a retracted position within housing 174. When the operator moves collar 170 in the proximal direction, shaft 172 slides into housing 174 and along with it the outer sleeve of cannula 120 and fluid ports 130 and 230 move together. FIG. 3 show a syringe 330 used to supply fluid, such as saline, through a fluid lumen within cannula 120 via tubing 332 and fluid port 230. According to some embodiments, the system 100 is formed of a single use portion 102 and a multiple use portion 104. The portions 102 and 104 are connectable and separable via a mechanical and electrical connector. According to some embodiments the cannula 120 is semi-rigid. The cannula 120 is stiff enough so it does not collapse with the longitudinal pushing and pulling forces of positioning a stent. On the other hand, cannula 120 is flexible enough such that it can bend while it passes through curved anatomy such as male urethra.

Figure 4:
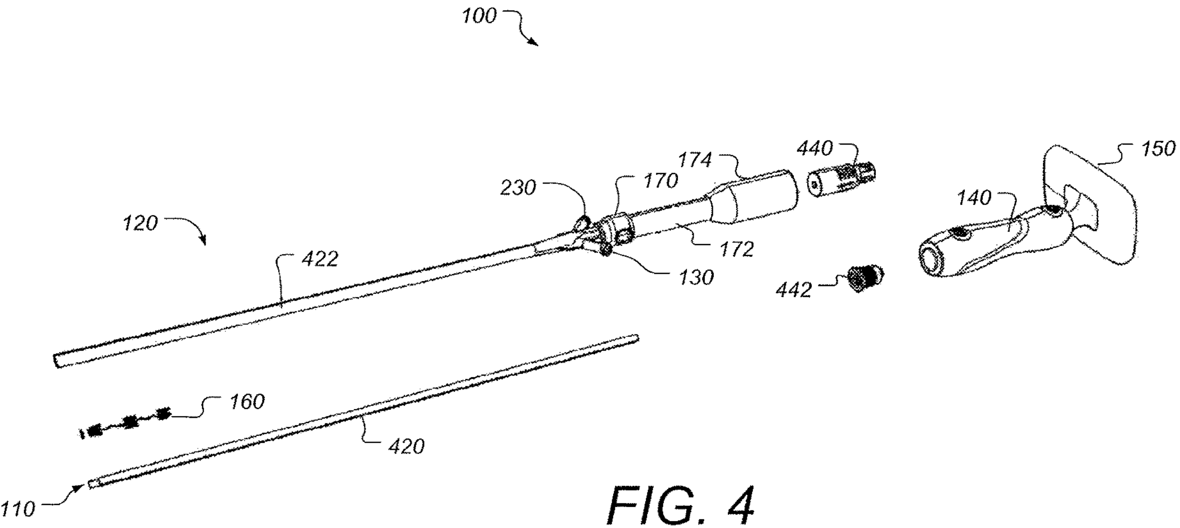
FIG. 4 is an exploded-view diagram of an endoscopic system configured to deploy a surgical stent, according to some embodiments.

FIG. 4 is an exploded-view diagram of an endoscopic system configured to deploy a surgical stent, according to some embodiments. The inner cannula 420 and outer sleeve 422 of cannula 120 are shown. The inner cannula 420 and distal tip 110 reside within and slide relative to the outer sleeve 422. The stent 160, prior to deployment, is disposed in the annular region between the inner cannula 420 and the outer sleeve 422. Also shown is connector 440 that fits in the proximal end of shaft 172 on the single use portion, and connector 442 that fits in the distal end of hand piece 140. According to some embodiments, stent 160 is of a type that can be used to open up the urethra. The stent 160 can be made of nitinol. When expanded, the stent pushes back the surrounding tissue and widens the urethra. Outer sleeve 422 has a smooth exterior, and is made of Nylon or PTFE, and can be coated with a hydrophilic material to enhance its smoothness.

Figures 5A, 5B, 5C:
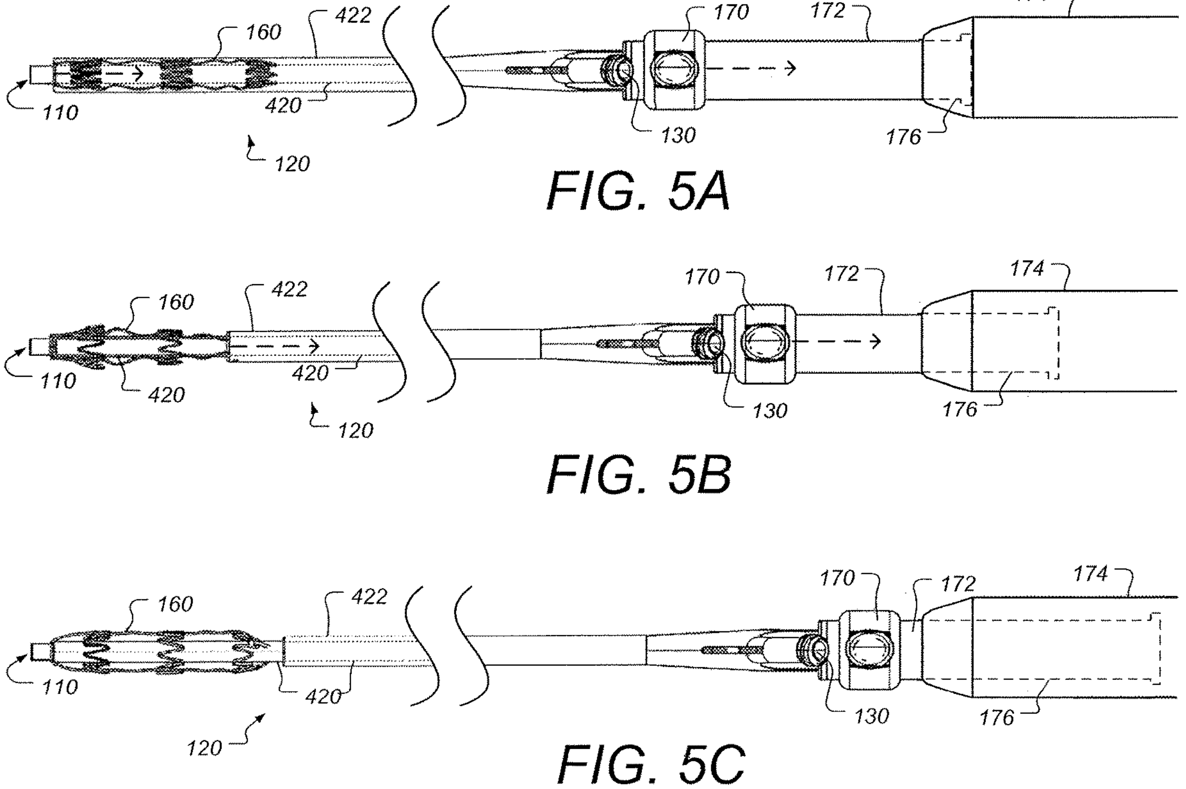
FIGS. 5A-5C are diagrams illustrating the operation of deploying a surgical stent using an endoscopic system, according to some embodiments.

FIGS. 5A-5C are diagrams illustrating the operation of deploying a surgical stent using an endoscopic system, according to some embodiments. The cannula 120 has an outer sleeve 422 concentrically positioned around inner cannula 420. FIG. 5A shows the stent 160 in a compressed state positioned between the inner cannula 420 (shown in dotted outline) and the outer sleeve 422. The stent 160 is formed to be stable in an expanded state (shown in FIG. 7B) such that when it is compressed, as in the position shown in FIG. 5A, the stent 160 is secured by friction while it being held in the compressed stated by the inner surface of outer sleeve 422. Collar 170, shaft 172 and fluid port 130 are attached to the outer sleeve 422 such that those components slide longitudinally. As outer sleeve 422 is retracted proximally, a portion of shaft 172 moves into housing 174 as shown by the dashed outline 176. As shown in FIG. 5B, the collar 170 and shaft 172 are partially moved proximally (shown by the dashed arrows) and the outer sleeve 422 is retracted by the same longitudinal distance. On the other hand, the inner cannula 420 and distal tip 110 are fixed to housing 174 such that they do not move when the collar 170, shaft 172 and outer sleeve 422 are retracted proximally. The stent 160 is prevented from moving proximally either by friction alone or by a means of its distal tip fitting around a flange on the distal end of inner cannula 420. Alternatively or in addition, one or more radial projections from inner cannula 420 that are just proximal of stent 160 can help keep the stent from moving proximally along inner cannula 420. When the collar 170, shaft 172 and sleeve 422 are retracted proximally, as shown in FIG. 5B, the portion of stent 160 that is no longer being restrained by sleeve 422 is allowed to expand. FIG. 5C shows the collar 170, shaft 172 and sleeve 422 fully retracted proximally. In this position, no portion of the stent 160 is restricted by the outer sleeve 422 and the stent is free to expand into the available surrounding space.

Figure 5D:
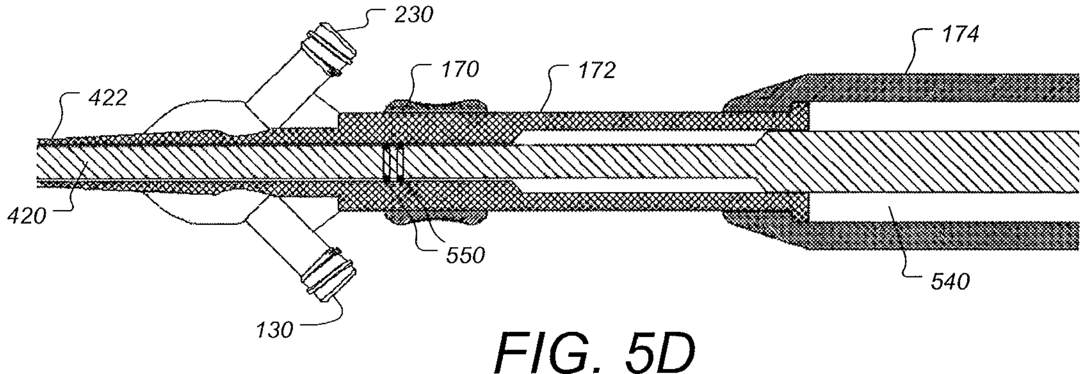
FIG. 5D is diagram illustrating a design for a sliding outer sleeve, according to some embodiments.

FIG. 5D is diagram illustrating a design for a sliding outer sleeve, according to some embodiments. As can be seen, collar 170, shaft 172 and fluid ports 130 and 230 are attached to the outer sleeve 422 such that those components slide longitudinally together. The shaft 172 fits inside of an annular space 540 within housing 174. According to some embodiments, o-rings 550 are provided to form a fluid seal which prevents fluid in the annular space between inner cannula 420 and outer sleeve 422 from leaking in a proximal direction.

Figure 6A:
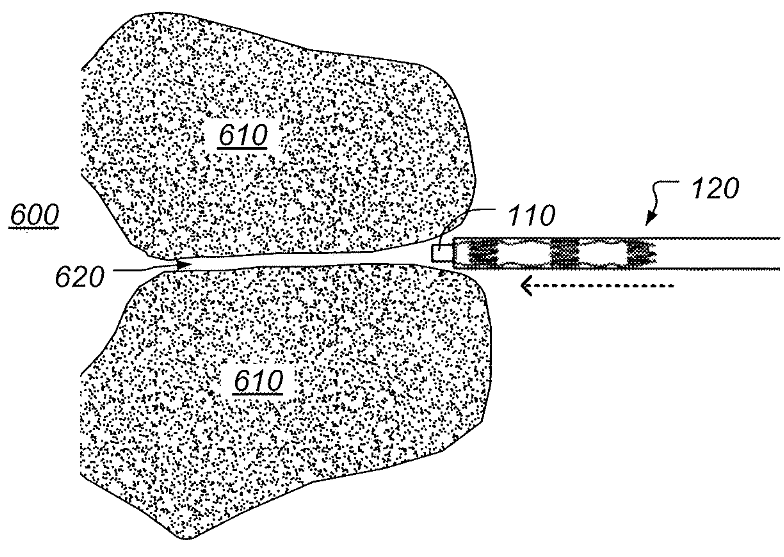
FIGS. 6A-6F are a series of diagrams illustrating a process of positioning and deploying a prostatic stent in a male urethra, according to some embodiments.
Figure 6B:
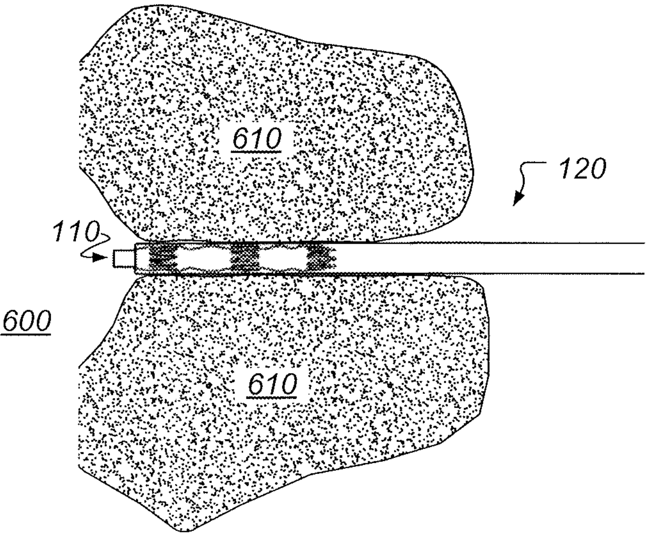
Figure 6C:
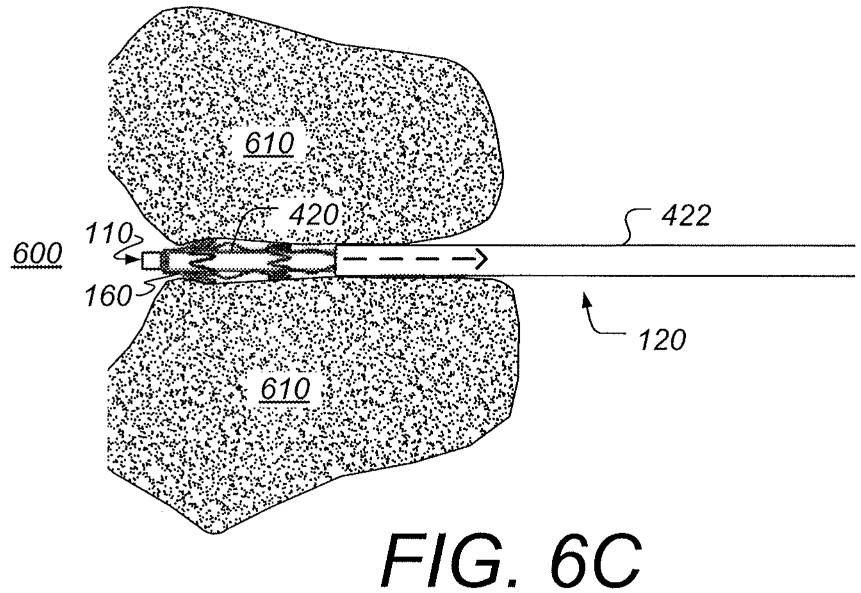
Figure 6D:
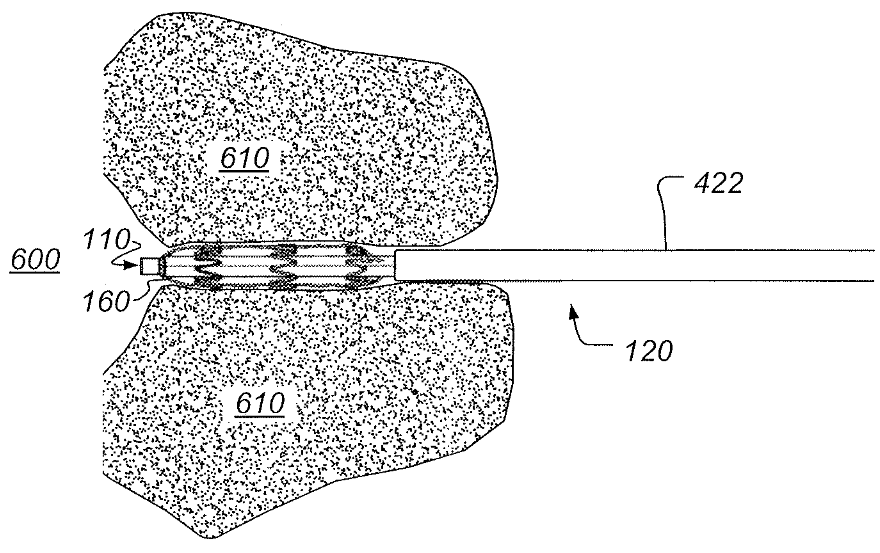

FIGS. 6A-6F are a series of diagrams illustrating a process of positioning and deploying a prostatic stent in a male urethra, according to some embodiments. In FIG. 6A, under direct vision of live video captured by the camera module in distal tip 110 and displayed to the operator on display 150 (shown in FIGS. 1-4) the cannula 120 is slowly advanced through the urethra towards prostate 610 and bladder 600. In FIG. 6B, the cannula 120 is shown inserted through the prostate canal 620 until the tip 110 reaches the entrance or neck of bladder. The precise location of the stent 160 with respect to the "neck" of bladder 600 and prostate canal 620 can be verified by the operator through the live images captured by the camera module in distal tip 110 and displayed to the operator on display 150 (shown in FIGS. 1-4). According to some embodiments, a distending media such as saline or $CO_2$ gas can flow through cannula 120 from either port 130 or 230 (e.g. shown in FIGS. 2 and 3) on the proximal end to the distal end, for example through the annular space between the inner cannula 420 and outer sleeve 422. In FIG. 6C, the outer sleeve 422 is slowly retracted while maintaining the longitudinal position of distal tip 110, inner cannula 420 and stent 160. This can be accomplished by the operator by maintaining the position of the hand piece 140 while slowly sliding the collar 170 proximally along shaft 172 (as shown in FIG. 5B). As the sleeve 422 is retracted, the portion of stent 160 that is no longer being restrained by sleeve 422 is allowed to expand against the walls of prostate canal 620. The sleeve 422 is retracted further until the distal end of the sleeve 422 is proximal to the proximal end of stent 160, as shown in FIG. 6D, such that the entire length of stent 160 is exposed.

Figure 6E:
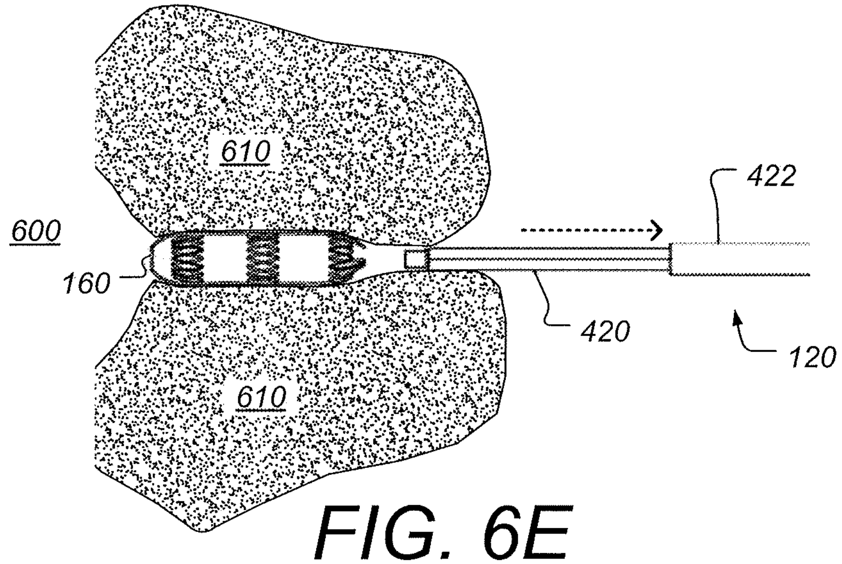
Figure 6F:
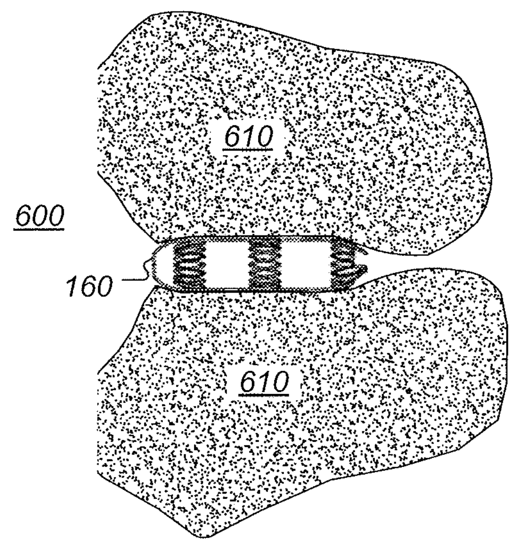
Figure 11A:
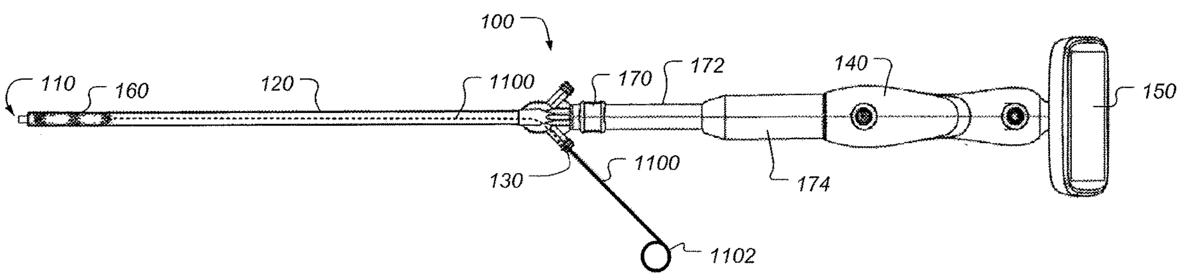
FIGS. 11A-11C are diagrams illustrating further detail of a wire or rod used aid in deployment of a surgical stent, according to some embodiments.
Figure 11B:
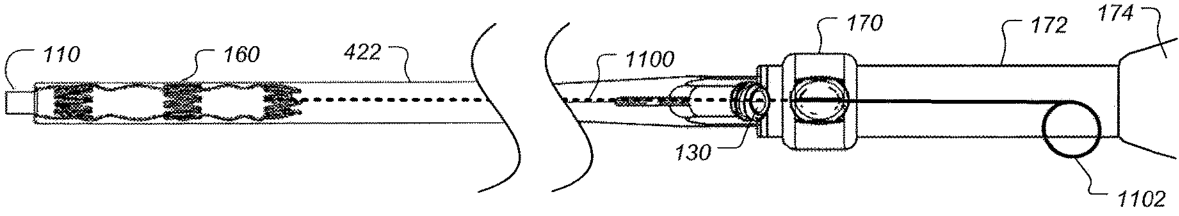
Figure 11C:
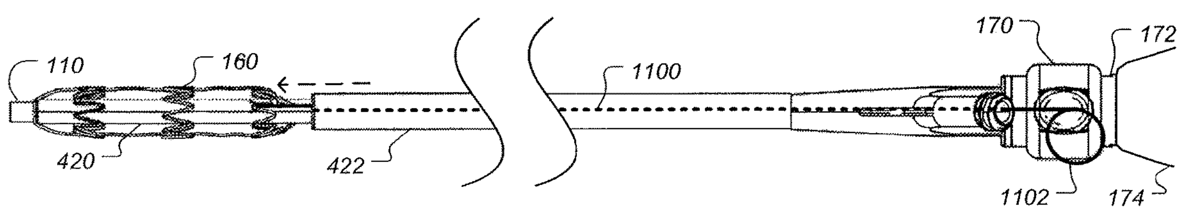

In FIG. 6E the cannula 120 is being withdrawn from the urethra as shown by the dotted arrow. The stent remains positioned in the prostate canal since it is pressed against the prostate canal wall. As the cannula 120 is slowly withdrawn, the correct positioning of the stent 160 can be verified by the operator through the live images captured by the camera module in distal tip 110 and displayed to the operator on display 150 (shown in FIGS. 1-4). The operator accomplishes this by sliding the collar 170 along shaft 172 to its most proximal position as shown in FIG. 5C. The stent 160 is now free to expand toward its stable expanded shape thereby exerting outward radial pressure on the prostate canal wall. According to some embodiments, a pusher wire or stick can be used, as shown in FIGS. 11A-11C to ensure release of the stent 160 from inner cannula 420 and to ensure proper positioning of stent 160. FIG. 6F shows the stent 160 expanded against the prostate canal wall after deployment.

Figure 7A:
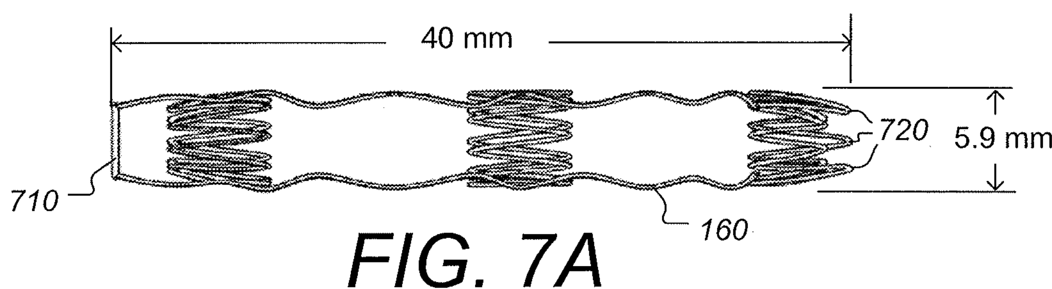
FIGS. 7A and 7B are side views of an endoscopically deployable surgical stent in compressed and expanded states, according some embodiments.
Figure 7B:
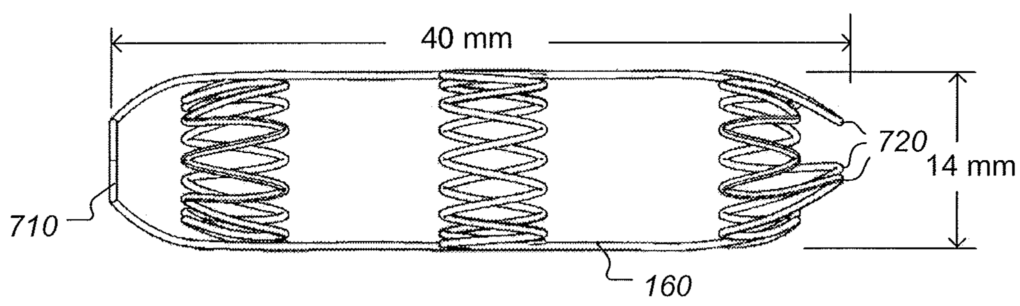

FIGS. 7A and 7B are side views of an endoscopically deployable surgical stent in compressed and expanded states, according some embodiments. FIG. 7A shows the example stent 160 in a compressed state, such as when it is positioned between the outer sleeve 422 and inner cannula 420 as shown in FIG. 5A. In this case the outer diameter of the stent is about 5.9 mm and the length is about 40 mm. FIG. 7B shows the example stent 160 in its expanded, relaxed, or stable state, such as shown in FIG. 5C. The length of the stent in its relaxed or expanded state is reduced to less than about 40 mm, for example to 20-30 mm, but the outer diameter is expanded to about 14 mm. According to some embodiments, stent 160 includes a ring 710 that is dimensioned to fit over the outer surface of the distal tip 110, which is some cases is about 3.8 mm O.D. but is smaller than the outer diameter of the inner cannula, as shown in greater detail in FIG. 10. Also visible in FIGS. 7A and 7B are proximal loops 720 on stent 160. According to some embodiments, loops 720 are shaped such as to be engageable by a suitable stent retrieval tool, such as shown in greater detail in FIGS. 12A-B and 13A-13E.

Figure 8:
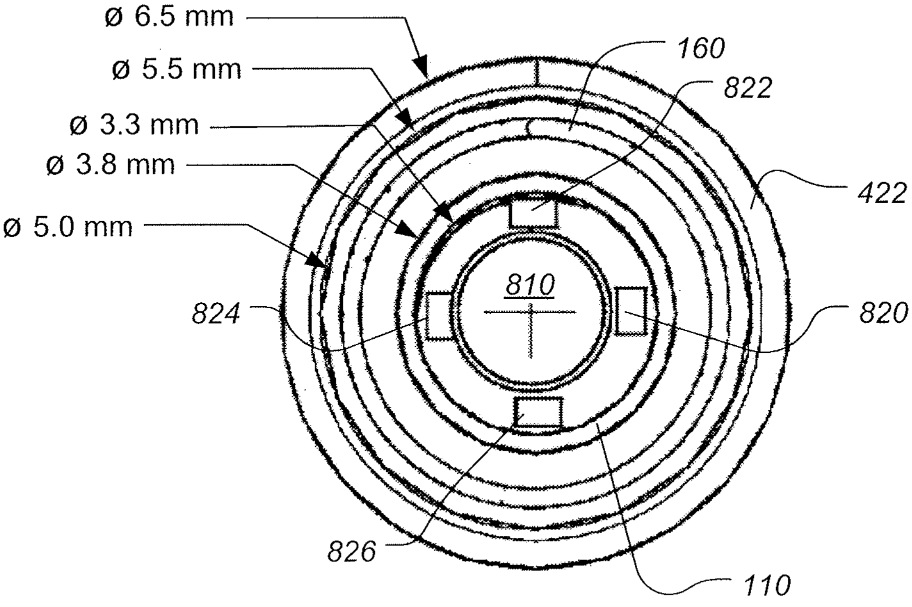
FIG. 8 shows further detail of the distal tip of an endoscopic system configured to deploy a surgical stent, according to some embodiments.

FIG. 8 shows further detail of the distal tip of an endoscopic system configured to deploy a surgical stent, according to some embodiments. The stent 160 is shown positioned between the inner cannula and outer sleeve 422. The distal ring 710 of stent 160 is shown around the distal tip 110. The distal tip is shown to include camera module 810 and four LEDs 820, 822, 824 and 826 all of which fit within a distal tip housing having an inner diameter of 3.3 mm and outer diameter of 3.8 mm. According to some embodiments, camera module 810 has field of view (FOV) at least 120 degrees and a fixed focal range of about 3 mm. According to various other embodiments, the fixed focal range camera module 810 ranges from less than 3 mm to about 30 mm. The outer sleeve 422 has an outer diameter of 6.5 mm and inner diameter of 5.5 mm. According to some embodiments, the outer diameter of the sleeve 422 can be made less than 6.5 mm. The stent 160 has a maximum outer diameter that matches (since it is constrained by) the inner diameter of sleeve 422. In the case shown in FIG. 8, the outer diameter of stent 160 is about 5.0 mm. According to some embodiments, the annular space or gap between the outer sleeve 422 and the inner cannula can be used for flow of distention fluid or gas. According to some embodiments, the outer sleeve 422 is formed of PTFE. The inner cannula 420 can also be formed of PTFE and can have an outer diameter of about 3.8 mm. The exterior of the outer sleeve can be coated with a hydrophilic material that becomes very slippery when wet during the medical procedure.

According to some embodiments, depending on the size of the camera module 810, the outer diameter of sleeve 422 can be made even less than 6.5 mm. In one example, the sleeve 422 has an outer diameter of 6.0 mm and an inner diameter of 4.9 mm. In this case the housing of distal tip 110 which includes camera module 810 and LEDs 820, 822, 824 and 826, has an inner diameter of 2.4 mm and outer diameter of 2.9 mm. The stent 160 in this case fits within the inner diameter of sleeve 422 and is has 4.0 mm outer diameter while compressed. While these dimensions are preferred, other embodiments can use other dimensions.

Figures 9A, 9B:
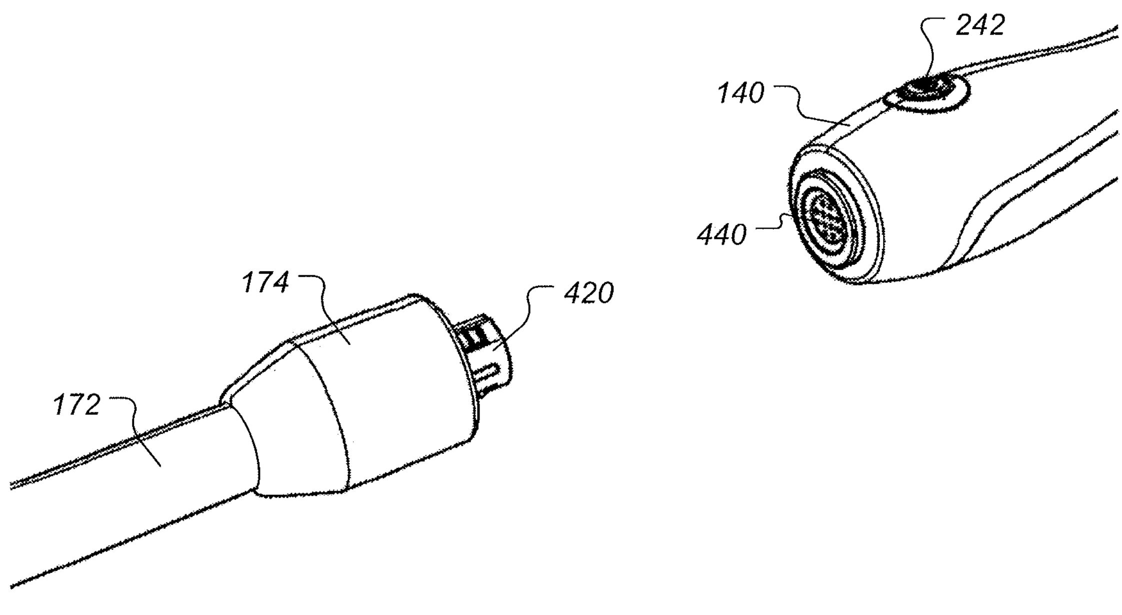
FIGS. 9A and 9B are perspective views showing further detail of connectors between single use and multiple use portions of an endoscopic system configured to deploy a surgical stent, according to some embodiments.

FIGS. 9A and 9B are perspective views showing further detail of connectors between single use and multiple use portions of an endoscopic system configured to deploy a surgical stent, according to some embodiments. The connector 420 has pins (not shown) that make electrical contact to sockets within connector 440 on the hand piece 140. According to some embodiments, the connectors 420 and 440 and mating collars surrounding them as illustrated are suitable for maintaining secure mechanical mating between the hand piece 140 of the multiple use portion (portion 104 shown in FIG. 1) and shaft 172 of the single use portion (portion 102 shown in FIG. 1).

Figure 10:
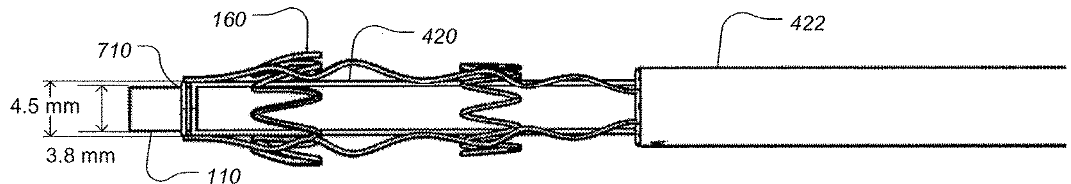
FIG. 10 is a side view showing further detail of the distal tip of an endoscopic system configured to deploy a surgical stent, according to some embodiments.

FIG. 10 is a side view showing further detail of the distal tip of an endoscopic system configured to deploy a surgical stent, according to some embodiments. In the example shown the outer diameter of the inner cannula 420 (about 4.5 mm) is slightly larger than the outer diameter of the distal tip 110 (about 3.8 mm). There is a slight “step” or “lip” formed by the diameter change and the ring 710 formed at the distal end of stent 160 is configured with an inner diameter between the two sizes so that it fits around the distal tip 110 but cannot slide further proximally past the lip/step formed by the distal end of the inner cannula 420. According to some other embodiments other dimensions can be used and/or the step can be formed on the housing of the distal tip itself or upon the body of the inner cannula. According to some other embodiments, there is no diameter change or step and the stent 160 is held in place by friction forces alone.

FIGS. 11A-11C are diagrams illustrating further detail of a wire or rod used aid in deployment of a surgical stent, according to some embodiments. Wire 1100 is shown running through port 130 and through cannula 120 toward stent 160. According to some embodiments, the wire 1100 is positioned in the annular space between the inner cannula the outer sleeve of cannula 120. The distal end of wire 1100 has a fork or other suitable shape that allows for engagement with a portion on the proximal end of stent 160. The wire is suitably stiff to allow for the operator to exert a pushing force, in the distal direction. During deployment, shown in FIG. 11C, when the outer sleeve 422 is retracted proximally, the operator can manipulate the handle loop 1102 of wire 1100 to push or urge the stent off of the end of the inner cannula 420 as shown by the dashed arrows. According to some embodiments, wire 1100 can thus be used to ensure precision placement of the stent 160.

Figure 12A:
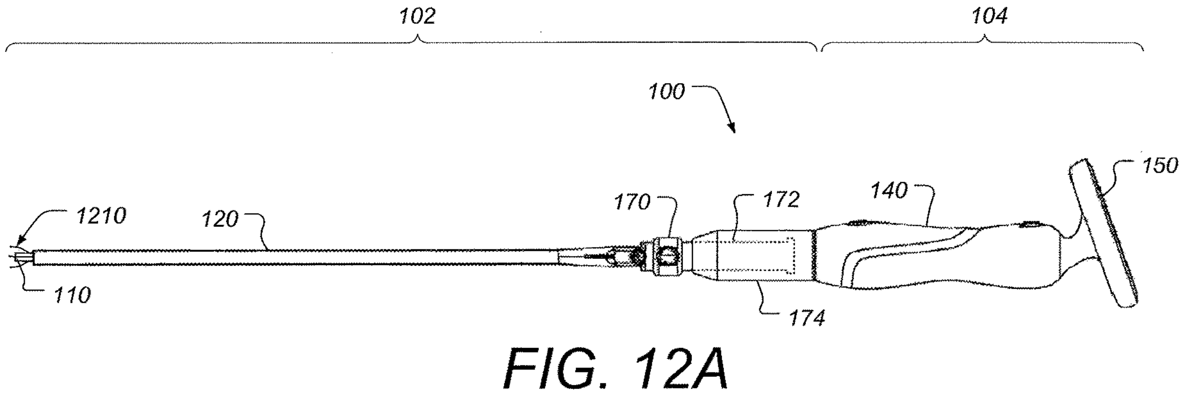
FIGS. 12A-12F are various views of an endoscopic system configured to remove a surgical stent, according to some embodiments.

FIGS. 12A-12F are various views of an endoscopic system configured to remove a surgical stent, according to some embodiments. In this example, the distal region of the system 100 is shown configured for stent removal. The distal tip 110 includes three retrieval hooks 1210 that protrude distally and are shaped to engage with proximal loops 720 of stent 160. The outer sleeve 422 can be used to surround the hooks so that the hooks 1210 are partially or fully enclosed within the sleeve 422. As shown in FIG. 12A, outer sleeve 422, collar 170 and shaft 172 are configured to allow sleeve 422 to protrude distally past the distal tip 110 and hooks 1210. The system 100 includes single use portion 102 and multiple use portion 104. According to some embodiments, the multiple use portion 104 is identical to the portion 104 shown in FIGS. 1-4, but the single use portion 102 shown in FIGS. 12A-E is customized for retrieval/removal of stents. In this case there can be two separate cannula versions, one for deployment and one for retrieval of stents, each of which can be separately mated to a single multiple use portion that includes the hand piece and display.

Figure 12B:
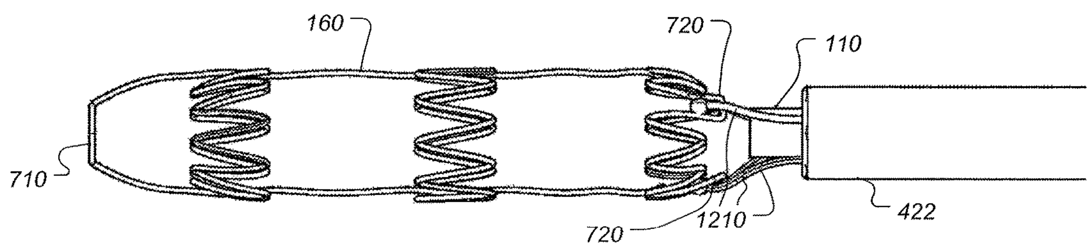
Figures 12C, 12D, 12E, 12F:
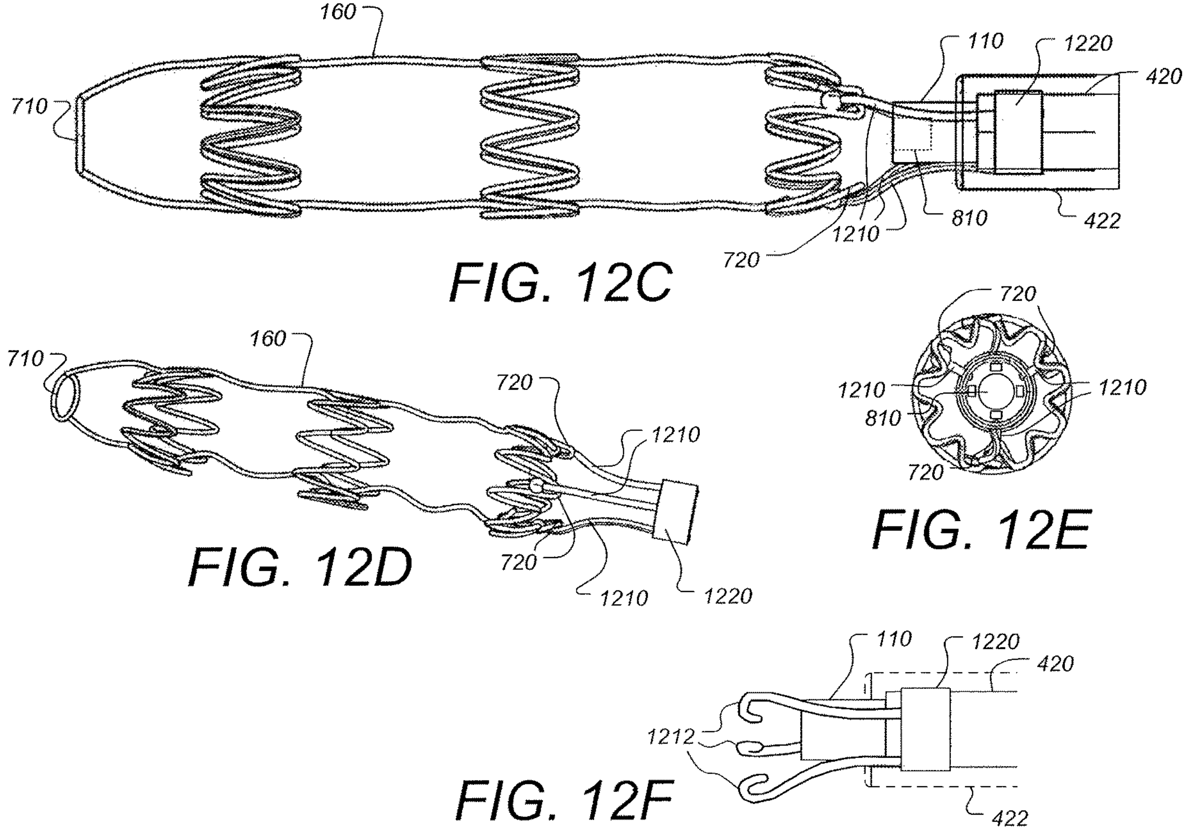
Figure 13A:
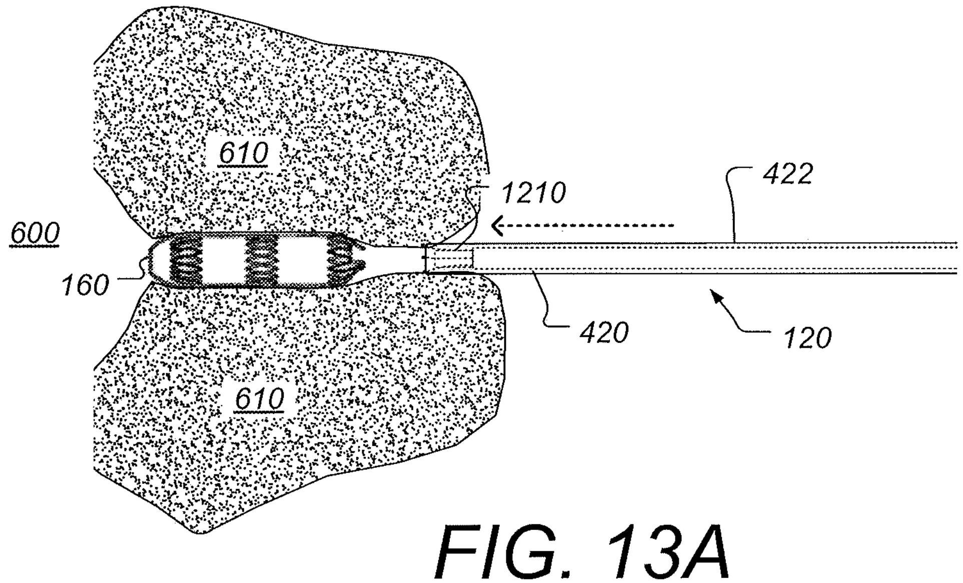
FIGS. 13A-13F are a series of diagrams illustrating methods for removing a prostatic stent from a male urethra, according to some embodiments.

The position shown in FIG. 12A is when the sleeve 422 is in a proximally retracted position. FIG. 12B shows further detail of the hooks 1210 engaged with the proximal loops 720 of stent 160. Moving the sleeve 422 in a longitudinal direction relative to hooks 1210 allows hooks 1210 to expand and contract radially. Note that partially or fully enclosing the hooks 1210 is desirable during insertion of the cannula 422 through the urethra, for example (as shown in FIG. 13A). FIGS. 12C and 12D show further detail of the distal tip region. According to some embodiments, hooks 1210 can be made of stainless steel and fixed (e.g. welded) to a steel band 1220 that can in-turn be fixed to the distal end of inner cannula 420. According to some embodiments, the inner cannula 420 is also made of stainless steel and band 1220 can be fixed to it by welding as well. FIG. 12E is a distal end view of the stent 160 being engaged by hooks 1210. Visible are the camera module 810 surrounded by LEDs on the distal tip of the retrieval device. According to some embodiments, other hook shapes can be used instead of a sphere on the end of a curved piece, as shown in FIGS. 128-E. For example, in FIG. 12F, the hooks 1212 are shaped more as traditional hooks which may be suitable for ensuring a secure engagement with the proximal end of the stent during the removal process.

Figure 13B:
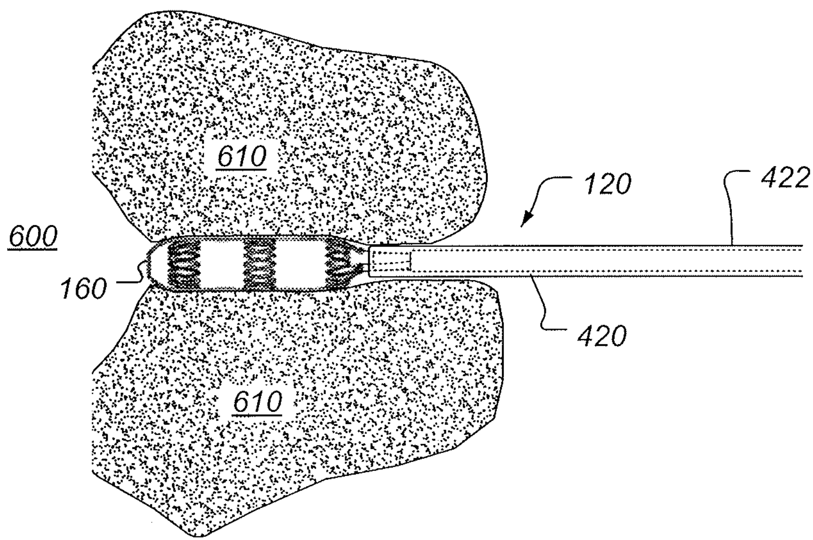
Figure 13C:
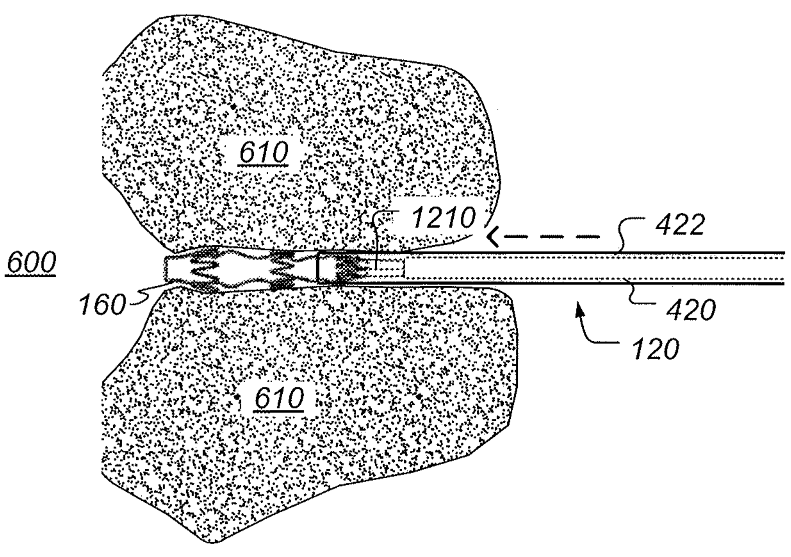
Figure 13D:
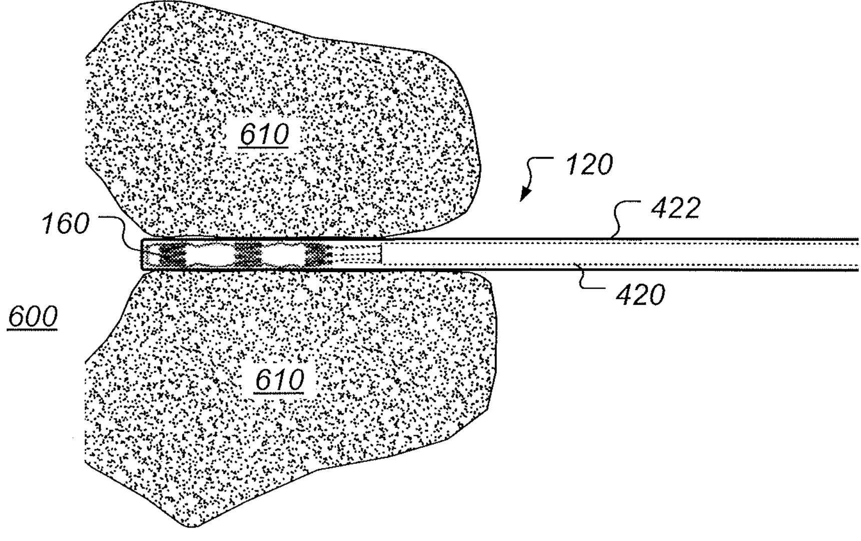
Figure 13E:
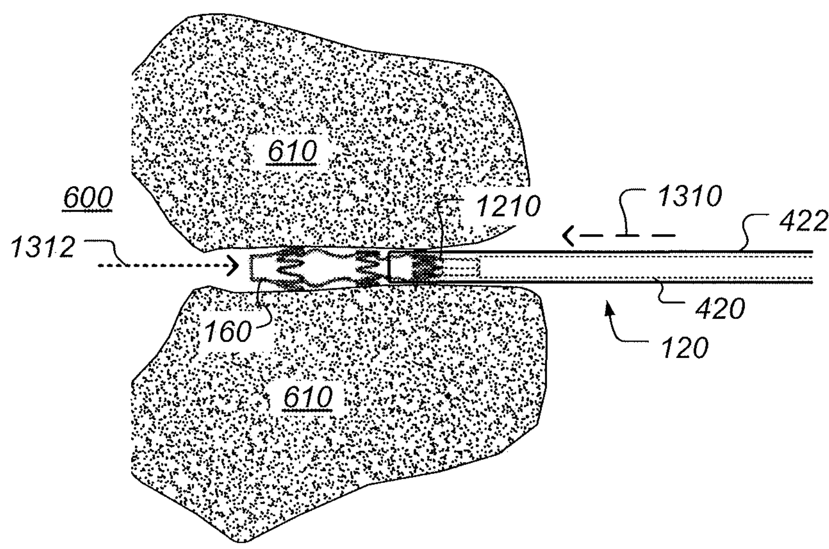
Figure 13F:
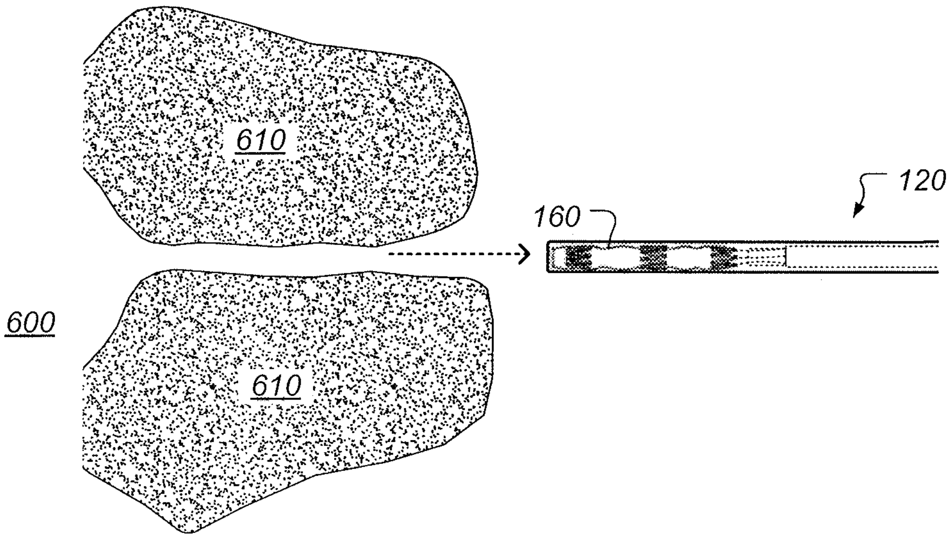

FIGS. 13A-13F are a series of diagrams illustrating methods for removing a prostatic stent from a male urethra, according to some embodiments. In FIG. 13A, the cannula 120 is inserted through the urethra as indicated by the dashed arrow. The retrieval hooks 1210 are fully or nearly fully enclosed by the outer sleeve 422. In FIG. 13B, the tip of hooks 1210 are shown in position to engage with the proximal loops on stent 160 (loops 720 shown in FIGS. 7A and 7B). The precise positioning of the hooks and engagement of the loops on the stent is ensured by direct vision-using live video images captured by the camera module 810 in this distal tip and displayed to the operator on the display screen 150. In FIG. 13C, once the engagement of the hooks 1210 on the loops of the stent 160 is confirmed, the outer sleeve 422 is pushed distally as shown by the dashed arrow while the hooks 1210, distal tip and inner cannula 420 remain in a static position. The sleeve 422 forces the stent 160 into a compressed state. This can be accomplished by the operator pushing the collar distally while maintaining a steady position on the hand piece. In FIG. 13D, the sleeve 422 is shown fully extended distally such that the stent 160 is fully enclosed and compressed by sleeve 422. In FIG. 13F, the cannula 120, with the stent 160 securely held in the compressed state, is withdrawn from the urethra. According to some embodiments, once the engagement of the hooks 1210 on the loops of the stent 160 is confirmed, instead of maintaining a steady position on the hand piece as shown in FIGS. 13C and 13D, a combination of pulling (proximally) on the hand piece and pushing on the collar (distally) can be used. This is shown in FIG. 13E where the inner cannula 420 hooks 1210 and stent 160 are being pulled proximally as shown by dotted arrow 1312 while the sleeve 422 is being pushed distally as shown by dashed arrow 1310. According to yet another embodiment, once the engagement of the hooks 1210 on the loops of the stent 160 is confirmed the sleeve 422 can be maintained in a static location relative to the target tissues (prostate 610) while the inner cannula 420 and hooks 1210 are used to pull the stent 160 in a proximal direction until it is partially or fully enclosed within the stationary sleeve 422. This can be accomplished by the operator simultaneously pulling (proximally) on the hand piece 140 (shown in FIG. 12A) while maintaining position relative to the patient's body on the collar 170 (shown in FIG. 12A).

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims.

What it claimed is:

1. A hand-held endoscope system comprising:

a handle configured to be grasped by a user;

a single-use stent deploying portion having a housing configured to removably attach to said handle and comprising:

a shaft extending from a distal end of the housing, the shaft having a proximal portion within an annular space of the housing so that the shaft moves between proximal and distal positions;

an outer sleeve extending distally from the shaft;

an inner cannula fixed to the housing and configured to fit within the outer sleeve for relative sliding motion directly therebetween;

a collar or catch coupled with the outer sleeve and configured to move together therewith between the distal position in which distal ends of the inner cannula and the outer sleeve align and the proximal position by which a distal portion of the inner cannula protrudes distally from the outer sleeve;

wherein said distal portion of the inner cannula and a distal portion of the outer sleeve are dimensioned to allow a radial space that is radially therebetween;

wherein said radial space is configured to constrain a radially expandable stent in a compressed state and said distal portion of the inner cannula is configured to engage the stent in said radial space to prevent proximal but not distal motion thereof relative to the inner cannula;

wherein said radial space matches the stent placed therein in length such that when the outer sleeve is at its proximal position the sleeve no longer constrains the stent from radial expansion to an expanded state for remaining in said passage; and a camera module at the distal end of said inner cannula;

a video screen attached to and mechanically supported by said handle and configured to show images taken with said camera module of the passage and of the stent being deployed therein; and mechanical and electrical connectors between said housing and said handle;

wherein the housing, shaft, collar, outer sleeve, and inner cannula form the single-use stent-deployment portion of the endoscope system, and the handle and video screen form a reusable portion, and said connectors are configured to release by hand, without tools, for disposal of said single-use portion after use thereof in a patient procedure.

2. The endoscope system of claim 1, further comprising a single-use stent removal portion configured to removably attach to said handle and comprising: a second outer sleeve and a second cannula therein that has a distal part equipped with plural hooks configured to fit in a radial space that is radially between the second inner cannula and the second outer sleeve when the second outer sleeve is at an axially distal position relative to the handle and to expand radially when the second outer sleeve is at an axially proximal position relative to the handle and to engage loops of a stent.

3. The endoscope system of claim 2, in which said stent removal portion is configured to draw a stent proximally into said radial space between the second outer sleeve and the second inner cannula when the second outer sleeve moves from its distal to its proximal positions relative to the handle.

4. The endoscope system of claim 1, in which said inner cannula is in a fixed position relative to the handle when said single-use portion and handle are assembled into said endoscope system.

5. The endoscope system of claim 1, further including proximal and distal ports in said outer sleeve and a fluid conduit through which fluid moves within and along a length of said outer sleeve between said ports.

6. The endoscope system of claim 1, in which said inner cannula has a distal end stepped down in diameter to engage a matching diameter distal end of a stent to thereby prevent proximal motion but allow distal motion of a stent relative to the inner cannula.

7. The endoscope system of claim 1, in which at least distal portions of the outer sleeve and the inner cannula are sufficiently flexible to bend while being inserted in curving portions of said passage.

8. A hand-held endoscope system comprising:

a handle configured to be grasped by a user;

a single-use stent deploying portion having a housing configured to removably attach to said handle and comprising:

a shaft extending from a distal end of the housing, the shaft having a proximal portion within an annular space of the housing so that the shaft moves between proximal and distal positions;

an outer sleeve extending distally from the shaft;

an inner cannula fixed to the housing and configured to fit directly within the outer sleeve;

said outer sleeve being configured to move relative to the housing and the inner cannula between the distal position and the proximal position;

wherein when the outer sleeve is in its proximal position a distal portion of the inner cannula protrudes distally from the outer sleeve and when the outer sleeve is in its distal position a tubular stent fits in a radial space that is radially between distal portions of the outer sleeve and the inner cannula; and a camera module at the distal end of said inner cannula;

a video screen attached to and mechanically supported by said handle and configured to show images taken with said camera module of the passage and of the stent being deployed therein; and mechanical and electrical connectors between said housing and said handle;

wherein the housing, shaft, outer sleeve and cannula form the single-use stent-deployment portion of the endoscope system, and the handle and video screen form a reusable portion, and said connectors release by hand, without tools, for disposal of said single-use portion after use thereof in a patient procedure.

9. The endoscope system of claim 8, further comprising a single-use stent removal portion that is configured to removably attach to said handle and comprises a second inner cannula and a second outer sleeve surrounding at least an axial extent of the second inner cannula, wherein the second inner cannula has plural hooks at a distal end thereof, which hooks are configured to fit in the second outer sleeve when the second outer sleeve is in a distal position relative to the second canula and to expand radially when the second outer sleeve is in a proximal position relative to the second cannula and to engage loops at a proximal portion of the stent.

10. The endoscope system of claim 9, in which said stent removal portion is configured to draw the stent proximally into said outer sleeve as the second outer sleeve moves from its proximal to its distal position relative to the second inner cannula.

11. The endoscope system of claim 8, further including proximal and distal ports in said outer sleeve and a fluid conduit through which fluid moves within and along a length of said outer sleeve between said ports.

12. The endoscope system of claim 8, in which said inner cannula has a distal end stepped down in diameter to engage a matching diameter distal end of a stent to thereby prevent proximal motion but allow distal motion of the distal end of a stent relative to the inner cannula.

13. The endoscope system of claim 8, in which at least distal portions of the outer sleeve and the inner cannula are sufficiently flexible to bend when being inserted in curving portions of said passage.

14. A method of deploying a stent in a passage in a patient, comprising:

placing a tubular stent in a compressed state in a radial space that is radially between distal portions of an inner cannula and an outer sleeve of an endoscope such that the stent engages the inner cannula to prevent proximal motion but enable distal motion of the stent relative to the inner cannula;

releasably securing said outer sleeve and inner cannula to an assembly defined by a shaft and a housing, wherein the housing is configured to be removably attached to a handle, wherein the outer sleeve extends distally from the shaft and includes a proximal portion within an annular space of the housing so that the shaft slides between proximal and distal positions, and wherein the inner cannula is fixed to the housing;

inserting the outer sleeve in a passage in the patient's body, with the stent in said radial space between the outer sleeve and the inner cannula;

sliding the outer sleeve directly over the inner cannula, proximally relative to the inner cannula, the stent, and the handle to thereby free the stent of being radially inwardly constrained by the outer sleeve and allow the stent to expand radially outwardly to an expanded state and remain in the passage in the patient;

withdrawing the inner cannula and the outer sleeve from the patient; and imaging the passage with a video camera at a tip of the inner cannula while inserting the outer sleeve, moving the outer sleeve proximally relative to the inner cannula, and withdrawing the inner cannula and outer sleeve, and displaying the images on a video screen secured to and mechanically supported by said handle.

15. The method of claim 14, including connecting said outer sleeve, inner cannula, and housing to said handle through electrical and mechanical connectors that connect and disconnect by hand, without tools.

16. The method of claim 14, further including removing a stent that has expanded radially and has remained in the passage by inserting a second outer sleeve into the passage while viewing the passage with a second video camera at a distal tip of a second inner cannula that is in the second outer sleeve, wherein the second outer sleeve and the second inner cannula are releasably attached to said handle, moving the second outer sleeve proximally relative to the second inner cannula to enable hooks secured to the second inner cannula to expand radially outwardly, engaging loops at a proximal portion of the stent with said hooks, moving one or both of the second inner cannula and the second outer sleeve relative to the other to draw the stent into a radial space that is radially between distal portions of the second outer sleeve and the second inner cannula, and withdrawing the second outer sleeve, the second inner cannula, and the stent from the passage.

17. The method of claim 14, further including removing a stent that has expanded radially outwardly and has remained in the passage by inserting a second outer sleeve into the passage while viewing the passage with a second video camera at a distal tip of a second inner cannula that is in the second outer sleeve, wherein said second outer sleeve and second cannula are releasably attached to said handle, moving the second outer sleeve proximally relative to the second inner cannula to allow hooks secured to the second inner cannula to expand radially outwardly, engaging loops at a proximal portion of the stent with said hooks, and moving said second inner cannula proximally relative to the passage to remove said stent from the passage.

* * * * *